(12) United States Patent
Cheng et al.

(10) Patent No.: US 10,428,085 B2
(45) Date of Patent: Oct. 1, 2019

(54) ASYMMETRIC BENZOTRICHALCOGENOPHENE COMPOUND AND POLYMER

(71) Applicant: NATIONAL CHIAO TUNG UNIVERSITY, Hsinchu (TW)

(72) Inventors: Yen-Ju Cheng, Taipei (TW); Yu-Chieh Pao, Taoyuan (TW); Shi-Yen Chen, Taipei (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 16/116,944

(22) Filed: Aug. 30, 2018

(65) Prior Publication Data

US 2018/0370986 A1 Dec. 27, 2018

Related U.S. Application Data

(62) Division of application No. 15/586,241, filed on May 3, 2017, now Pat. No. 10,093,680.

(30) Foreign Application Priority Data

Feb. 20, 2017 (TW) .............................. 106105628 A

(51) Int. Cl.
| | | |
|---|---|---|
| *C07D 495/14* | (2006.01) | |
| *C07D 517/14* | (2006.01) | |
| *C08G 79/00* | (2006.01) | |
| *C08G 61/12* | (2006.01) | |
| *H01L 51/00* | (2006.01) | |
| *H01L 51/42* | (2006.01) | |

(52) U.S. Cl.
CPC ......... *C07D 495/14* (2013.01); *C07D 517/14* (2013.01); *C08G 61/123* (2013.01); *C08G 61/124* (2013.01); *C08G 61/126* (2013.01); *C08G 79/00* (2013.01); *H01L 51/0036* (2013.01); *H01L 51/0043* (2013.01); *C08G 2261/122* (2013.01); *C08G 2261/1412* (2013.01); *C08G 2261/3223* (2013.01); *C08G 2261/3241* (2013.01); *C08G 2261/3243* (2013.01); *C08G 2261/3244* (2013.01); *C08G 2261/3246* (2013.01); *C08G 2261/411* (2013.01); *C08G 2261/414* (2013.01); *C08G 2261/91* (2013.01); *C08G 2261/92* (2013.01); *H01L 51/4253* (2013.01)

(58) Field of Classification Search
CPC ........ H01M 14/00; C09B 57/00; H01L 31/04; C07D 495/14; C07F 7/22
USPC .............. 252/299.61, 299.62, 500; 548/445; 549/42, 43
See application file for complete search history.

(56) References Cited

U.S. PATENT DOCUMENTS 9,359,470 B2 * 6/2016 Welker .................... C09B 57/00
2013/0334520 A1 12/2013 Amb et al.

FOREIGN PATENT DOCUMENTS

| CN | 103172837 A | 6/2013 |
| CN | 103288848 A | 9/2013 |
| CN | 104119516 A | 10/2014 |
| CN | 104211923 A | 12/2014 |
| JP | 2011-006388 A | 1/2011 |
| JP | 2011-222373 A | 11/2011 |

OTHER PUBLICATIONS

Hayato Tsuji et al., "Synthesis of Benzotrifuran and Benzotripyrrole Derivatives and Molecular Orientations on the Surface and in the Solid State", Chemistry An Asian Journal, vol. 8, Oct. 2013, pp. 2377-2382.
Tomoya Kashiki et al., "One-pot Synthesis of Benzo[b]thiophenes and Benzo[b]selenophenes from o-Halo-Substituted Ethynylbenzenes: Convenient Approach to Mono-, Bis-, and Tris-Chalcogenophene-Annulated Benzenes", Organic Letters, vol. 10, No. 11, 2009, pp. 2473-2475.
Yohann Nicolas et al., "Planarized Star-Shaped Oligothiophenes with Enhanced π-Electron Delocalization", Organic Letters, vol. 6, No. 2, 2004, pp. 273-276.
Tyler Taerum et al., "Synthesis, Polymerization, and Unusual Properties of New Star-Shaped Thiophene Oligomers", Organic Letters, vol. 11, No. 15, 2009, pp. 3230-3233.
Christian B. Nielsen et al., "Benzotrithiophene—A Planar, Electron-Rich Building Block for Organic Semiconductors", Organic Letters, vol. 13, No. 9, 2011, pp. 2414-2417.
Asit Patra et al., "Planar [6]Radialenes: Structure, Synthesis, and Aromaticity of Benzotriselenophene and Benzotrithiophene", Angewandte Chemie International Edition, vol. 46, Nov. 26, 2007, pp. 8814-8818.
Xin Guo et al., "Making Benzotrithiophene a Stronger Electron Donor", Organic Letters, vol. 13, No. 22, 2011, pp. 6062-6065.
Stoichko D. Dimitrov et al., "Efficient Charge Photogeneration by the Dissociation of PC70BM Excitons in Polymer/Fullerene Solar Cells", J. Phys. Chem. Lett., 2012, pp. 140-144.

* cited by examiner

*Primary Examiner* — William K Cheung
(74) *Attorney, Agent, or Firm* — CKC & Partners Co., LLC

(57) ABSTRACT

An asymmetric benzotrichalcogenophene compound and a polymer are provided. The asymmetric benzotrichalcogenophene compound is a heterocyclic compound having furan, thiophene, selenophene and/or tellurophene subunits. The polymer has an asymmetric benzotrichalcogenophene subunit and can be formed by polymerizing the asymmetric benzotrichalcogenophene compound and an electron-accepting compound. The polymer may be used as a semiconductor active layer material in an organic field effect transistor or a heterogeneous interface material of an organic solar cell.

5 Claims, No Drawings

ASYMMETRIC BENZOTRICHALCOGENOPHENE COMPOUND AND POLYMER

RELATED APPLICATION

The present application is a Divisional Application of the U.S. application Ser. No. 15/586,241, filed May 3, 2017 now U.S. Pat. No. 10,093,680, which claims priority to Taiwan Application Serial Number 106105628, filed Feb. 20, 2017, all of which are herein incorporated by reference.

BACKGROUND

Field of Invention

The present invention relates to an asymmetric benzotrichalcogenophene compound, a synthesis method thereof, and a polymer having the asymmetric benzotrichalcogenophene subunit. More particularly, the present invention relates to an asymmetric benzotrichalcogenophene compound having a heterocyclic structure, in which the heterocyclic structure is a combination of furan, thiophene, selenophene and/or tellurophene subunits.

Description of Related Art

In general, star-shaped conjugated molecules formed by benzotrichalcogenophene (BTC) compound can serve as a semiconductor material, for example, organic field effect transistors (OFETs) and polymer solar cells (PSCs). The stacking ability of asymmetric benzotrichalcogenophene compound is higher than symmetric benzotrichalcogenophene compound, as well as the conjugate length and the conductivity. However, the currently known asymmetric benzotrichalcogenophene compound is benzotrithiophene.

In addition, the current symmetric benzotrichalcogenophene compound and asymmetric benzotrichalcogenophene compound include only a single type of chalcogenophene due to the difficulties of synthesis. It lacks of a benzotrichalcogenophene compound having two or more types of chalcogenophene. More specifically, the chalcogenophene includes furan, thiophene, selenophene and tellurophene, in which tellurophene is a stronger electron donor than furan, thiophene and selenophene. However, the reactivity and stability of tellurophene is weaker than furan, thiophene and selenophene, and therefore it is not easy to carry out the functionalization or further application of tellurophene. In addition, it lacks of a benzotrichalcogenophene compound having tellurophene with other chalcogenophene.

Accordingly, there is a need for an asymmetric benzotrichalcogenophene compound having two or more types of chalcogenophene, a synthesis method thereof, and a polymer having the asymmetric benzotrichalcogenophene subunit.

SUMMARY

The invention provides an asymmetric benzotrichalcogenophene compound having a structure of chemical formula (1):

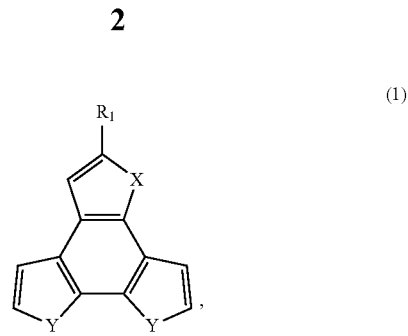

wherein $R_1$ is hydrogen, $-C_pH_{2p+1}$, $-COC_qH_{2q+1}$ or $-COOC_rH_{2r+1}$, p is an integer of 1~20, q is an integer of 1~12, r is an integer of 1~12; X is selected from the group consisting of oxygen, sulfur, selenium, tellurium, and a combination thereof; Y is selected from the group consisting of oxygen, sulfur, selenium, tellurium, and a combination thereof; when X is sulfur, Y is not sulfur.

In one embodiment, $-C_pH_{2p+1}$ is a linear structure or a branched structure.

In one embodiment, $-COC_qH_{2q+1}$ is a linear structure or a branched structure.

In one embodiment, $-COOC_rH_{2r+1}$ is a linear structure or a branched structure.

The present invention provides a synthesis method of an asymmetric benzotrichalcogenophene compound including steps of: mixing a first compound, a second compound, a zero-valent palladium catalyst, and a base to form a third compound, the first compound has a structure of chemical formula (2):

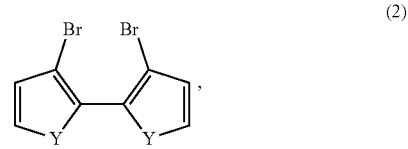

wherein Y is selected from the group consisting of oxygen, sulfur, selenium, tellurium, and a combination thereof; the second compound has a structure of chemical formula (3):

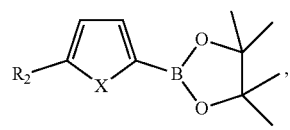

wherein X is selected from the group consisting of oxygen, sulfur, selenium, and tellurium, and a combination thereof; when Y is sulfur, X is not sulfur, $R_2$ is $-C_pH_{2p+1}$, p is an integer of 1~20; the third compound has a structure of chemical formula (4):

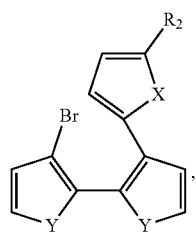

(4)

mixing the third compound with a divalent palladium catalyst to form the asymmetric benzotrichalcogenophene compound.

In one embodiment, the first compound, the second compound, the zero-valent palladium catalyst and the base are dissolved in an organic solvent.

In one embodiment, the zero-valent palladium catalyst is tetrakis(triphenylphosphine)palladium, $Pd(PPh_3)_4$.

In one embodiment, the base is selected from sodium carbonate or potassium carbonate.

In one embodiment, the third compound and the divalent palladium catalyst are dissolved in an organic solvent.

In one embodiment, the divalent palladium catalyst is [1,3-bis(2,6-diisopropylphenyl)imidazol-2-ylidene]chloro[3-phenylallyl]palladium(II), Pd-IPr.

The present invention provides a synthesis method of an asymmetric benzotrichalcogenophene compound including steps of: mixing a first compound, a second compound and a zero-valent palladium catalyst, the first compound has a structure of chemical formula (5):

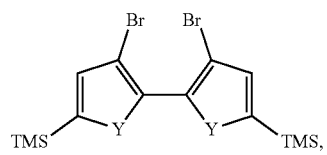

(5)

wherein Y is selected from the group consisting of oxygen, sulfur, selenium, tellurium, and a combination thereof; the second compound has a structure of chemical formula (6):

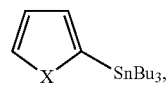

(6)

wherein X is selected from the group consisting of oxygen, sulfur, selenium, tellurium, and a combination thereof; when Y is sulfur, X is not sulfur; adding aluminium chloride and acyl chloride having substituent of $-COC_qH_{2q+1}$ or $-COOC_rH_{2r+1}$, wherein q is an integer of 1~12, r is an integer of 1~12; adding a quaternary ammonium salt to form a third compound, the third compound has a structure of chemical formula (7):

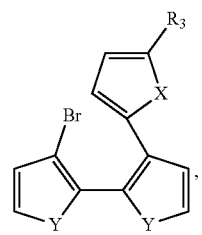

(7)

wherein $R_3$ is $-COC_qH_{2q+1}$ or $-COOC_rH_{2r+1}$, q is an integer of 1~12, r is an integer of 1~12; mixing the third compound and a divalent palladium catalyst to form the asymmetric benzotrichalcogenophene compound.

In one embodiment, the first compound, the second compound and the zero-valent palladium catalyst are dissolved in an organic solvent.

In one embodiment, the zero-valent palladium catalyst is tetrakis(triphenylphosphine)palladium, $Pd(PPh_3)_4$.

In one embodiment, the quaternary ammonium salt is tetrabutylammonium fluoride (TBAF).

In one embodiment, the third compound and the divalent palladium catalyst are dissolved in an organic solvent.

In one embodiment, the divalent palladium catalyst is [1,3-bis(2,6-diisopropylphenyl)imidazol-2-ylidene]chloro[3-phenylallyl]palladium(II), Pd-IPr.

The present invention provides a polymer having a structure of chemical formula (8):

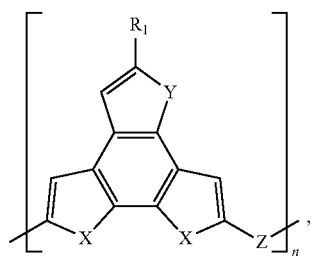

(8)

wherein $R_1$ is hydrogen, $-C_pH_{2p+1}$, $-COC_qH_{2q+1}$ or $-COOC_rH_{2r+1}$, p is an integer of 1~20, q is an integer of 1~12, r is an integer of 1~12, n is an integer of 10~100; X is selected from the group consisting of oxygen, sulfur, selenium, tellurium, and a combination thereof; Y is selected from the group consisting of oxygen, sulfur, selenium, tellurium, and a combination thereof; Z is selected from

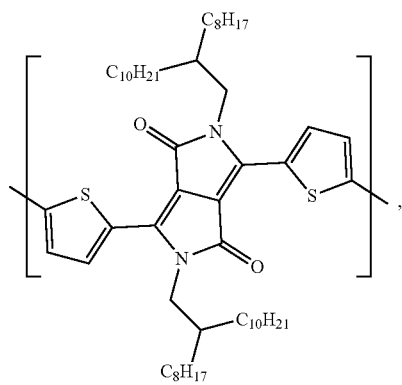

-continued

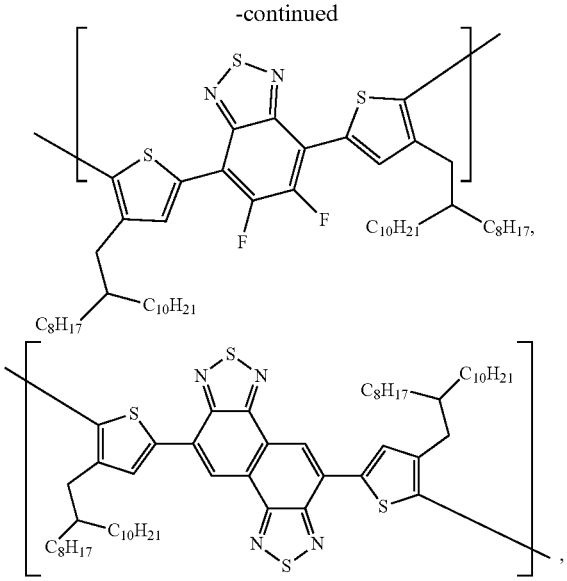

and a combination thereof.

In summary, the present invention provides an asymmetric benzotrichalcogenophene compound having two or more types of chalcogenophene and a synthesis method thereof. The present invention also provides a polymer having the asymmetric benzotrichalcogenophene subunit.

DETAILED DESCRIPTION

In order to make the description of the present invention more detailed and more comprehensive, various aspects and embodiments of the present invention are described below illustratively. However, these illustrated aspects and embodiments are not the only way for implementing or using the embodiments of the invention. The embodiments disclosed hereinafter may be combined with or replaced by each other under beneficial situations, and alternatively other embodiments may be appended to an embodiment, without any further statement or illustration. In the following description, many specific details are illustrated so that readers can understand the following embodiments completely. However, the embodiments of the present invention may also be implemented without these specific details.

The embodiment is described in details as follows, but the instant disclosure is not limited to the scope of the embodiment.

In some embodiments, an asymmetric benzotrichalcogenophene compound has a structure of chemical formula (1):

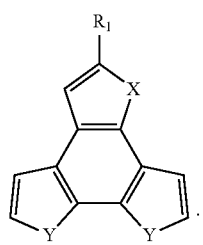

(1)

$R_1$ is hydrogen, $-C_pH_{2p+1}$, $-COC_qH_{2q+1}$ or $-COOC_rH_{2r+1}$. In one embodiment, $-C_pH_{2p+1}$, $-COC_qH_{2q+1}$ and $-COOC_rH_{2r+1}$ are independently a linear structure or a branched structure, p is an integer of 1~20, q is an integer of 1~12, and r is an integer of 1~12. X is selected from the group consisting of oxygen, sulfur, selenium, tellurium, and a combination thereof. Y is selected from the group consisting of oxygen, sulfur, selenium, tellurium, and a combination thereof. When X is sulfur, Y is not sulfur.

For example, a synthesis method of the aforementioned asymmetric benzotrichalcogenophene compound includes steps of mixing a first compound, a second compound, a zero-valent palladium catalyst, and a base to form a third compound. Specifically, the zero-valent palladium catalyst is used to catalyze the Suzuki coupling reaction of the first compound and the second compound to form a third compound. The first compound has a structure of chemical formula (2):

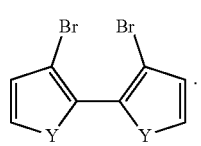 [SMILES: Brc1ccsc1-c1sccc1Br]

(2)

Y is selected from the group consisting of oxygen, sulfur, selenium, tellurium, and a combination thereof. The second compound has a structure of chemical formula (3):

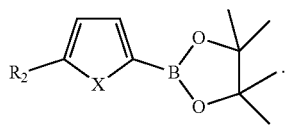

(3)

X is selected from the group consisting of oxygen, sulfur, selenium, tellurium, and a combination thereof. When Y is sulfur, X is not sulfur, $R_2$ is $-C_pH_{2p+1}$, and p is an integer of 1~20. The third compound has a structure of chemical formula (4):

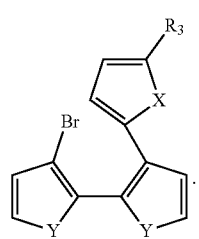

(4)

In one embodiment, the zero-valent palladium catalyst is tetrakis(triphenylphosphine)palladium, $Pd(PPh_3)_4$. In one embodiment, the base is selected from sodium carbonate ($Na_2CO_3$), potassium carbonate ($K_2CO_3$), and a combination thereof. In one embodiment, further includes dissolving the first compound, the second compound, the zero-valent palladium catalyst, and the base in an organic solvent. The organic solvent, for example, is selected from tetrahydrofuran (THF) or toluene. In one embodiment, a polar solvent is further added into the organic solvent. The polar solvent, for example, is water.

The asymmetric benzotrichalcogenophene compound is formed by mixing the third compound and a divalent palladium catalyst in succession. Specifically, the divalent palladium catalyst may catalyze the intramolecular cyclization reaction of the third compound.

In one embodiment, the divalent palladium catalyst is [1,3-bis(2,6-diisopropylphenyl)imidazol-2-ylidene]chloro[3-phenylallyl]palladium(II), Pd-IPr.

In one embodiment, pivalic acid and potassium carbonate are further added into the mixture while mixing the third compound and the divalent palladium catalyst. In one embodiment, an organic solvent is further added into the mixture while mixing the third compound and the divalent palladium. The organic solvent is dimethylacetamide (DMAc), for example. In one embodiment, a mixture comprising the third compound and the divalent palladium catalyst is heated to 90~150° C. to enhance the reaction rate of the formation of the asymmetric benzotrichalcogenophene compound.

Some asymmetric benzotrichalcogenophene compounds prepared by the aforementioned synthesis method are listed in Table 1:

TABLE 1

| Compound | Structure |
|---|---|
| 1-A | $C_{18}H_{37}$, with O, S, S ring system |
| 1-B | $C_{18}H_{37}$, with S, S, S ring system |
| 1-C | $C_{18}H_{37}$, with Se, S, S ring system |
| 1-D | $C_{18}H_{37}$, with Te, S, S ring system |

TABLE 1-continued

| Compound | Structure |
|---|---|
| 1-E | $C_{18}H_{37}$, with O, Se, Se ring system |
| 1-F | $C_{18}H_{37}$, with S, Se, Se ring system |
| 1-G | $C_{18}H_{37}$, with Se, Se, Se ring system |
| 1-H | $C_{18}H_{37}$, with Te, Se, Se ring system |

Examples 1-8 are given below to describe the details of the present embodiment. The reaction conditions for the synthesis of Compound 1-A to Compound 1-H are described respectively.

Example 1: Synthesis of Compound 1-A

The first compound in this example has a structure of:

The second compound in this example has a structure of:

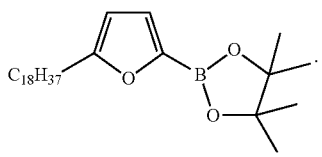

The third compound in this example has a structure of:

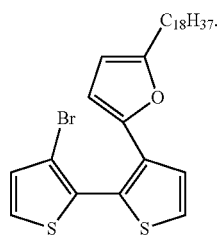

In this example, a degassed solution of the first compound (292 mg, 0.90 mmol), the second compound (403 mg, 0.90 mmol), Pd(PPh$_3$)$_4$ catalyst (52 mg, 5 mol %) and sodium carbonate (382 mg, 3.60 mmol) in THF/H$_2$O (25 mL/6 mL) was stirred for 17 h at 80° C. under N$_2$ atmosphere. After cooling to room temperature, the solution was extracted with ether, 20 mL each time for three times, and once with water (20 mL). The combined organic layer was dried over MgSO$_4$. After removal of the organic solvent under reduced pressure and a concentration process, the residue was purified by column chromatography on silica gel (hexane) to give a 297 mg liquid of third compound with yield rate of 58% and melting point of 48° C.

A degassed solution of the third compound (297 mg, 0.53 mmol), pivalic acid (16 mg, 0.16 mmol), Pd-IPr catalyst (17 mg, 5 mol %) and potassium carbonate (182 mg, 1.32 mmol) in DMAc (2 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure, the residue was purified by column chromatography on silica gel (hexane) to give a white solid of Compound 1-A (113 mg, yield rate=44%, melting temperature 71° C.).

Example 2: Synthesis of Compound 1-B

The first compound in this example has a structure of:

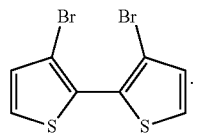 [SMILES: Brc1ccsc1-c1sccc1Br]

The second compound in this example has a structure of:

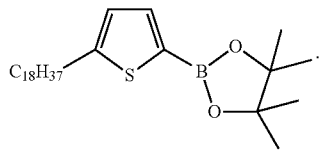

The third compound in this example has a structure of:

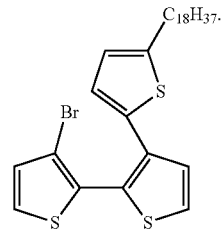

In this example, a degassed solution of the first compound (210 mg, 0.64 mmol), the second compound (300 mg, 0.64 mmol), Pd(PPh$_3$)$_4$ catalyst (37 mg, 5 mol %) and sodium carbonate (275 mg, 2.59 mmol) in THF/H$_2$O (19 mL/5 mL) was stirred for 17 h at 80° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (113 mg, yield rate=30%, melting temperature 57° C.).

A degassed solution of the third compound (280 mg, 0.48 mmol), pivalic acid (15 mg, 0.14 mmol), Pd-IPr catalyst (16 mg, 5 mol %) and K$_2$CO$_3$ (167 mg, 1.21 mmol) in DMAc (2 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-B (143 mg, yield rate=59%, melting temperature=65° C.).

Example 3: Synthesis of Compound 1-C

The first compound in this example has a structure of:

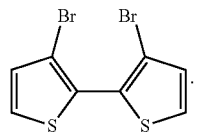 [SMILES: Brc1ccsc1-c1sccc1Br]

The second compound in this example has a structure of:

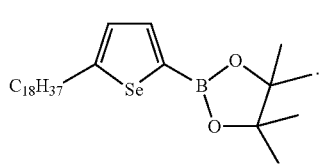

The third compound in this example has a structure of:

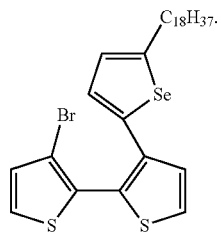

In this example, a degassed solution of the first compound (1100 mg, 2.16 mmol), the second compound (700 mg, 2.16 mmol), Pd(PPh$_3$)$_4$ catalyst (125 mg, 5 mol %) and Na$_2$CO$_3$ (915 mg, 8.63 mmol) in THF/H$_2$O (62 mL/15 mL) was stirred for 17 h at 80° C. under N$_2$ atmosphere. After cooling to room temperature, the solution was extracted with ether, 30 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of third compound (600 mg, yield rate=44%, melting temperature=48° C.).

A degassed solution of the third compound (500 mg, 0.80 mmol), pivalic acid (24 mg, 0.24 mmol), Pd-IPr catalyst (26 mg, 5 mol %) and K$_2$CO$_3$ (276 mg, 1.99 mmol) in DMAc (3.5 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-C (330 mg, yield rate=76%, melting temperature=71° C.).

The third compound in this example has a structure of:

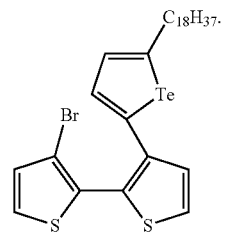

In this example, a degassed solution of the first compound (300 mg, 0.93 mmol), the second compound (551 mg, 0.93 mmol), Pd(PPh$_3$)$_4$ catalyst (53 mg, 5 mol %) and triphenylphosphine (24 mg, 0.09 mmol) in toluene (9 mL) was stirred for 17 h at 110° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (155 mg, yield rate=25%, melting temperature=50° C.).

A degassed solution of the third compound (132 mg, 0.20 mmol), pivalic acid (6 mg, 0.06 mmol), Pd-IPr catalyst (19 mg, 15 mol %) and K$_2$CO$_3$ (68 mg, 0.49 mmol) in DMAc (1 mL) was stirred for 17 h at 120° C. under N$_2$ atmosphere. After cooling to room temperature, the solution was extracted with ether, 10 mL each time for three times, and once with water (10 mL). The combined organic layer was dried over MgSO$_4$. After removal of the organic solvent under reduced pressure and a concentration process, the residue was purified by column chromatography on silica gel (hexane) to give a white solid of Compound 1-D (79 mg, yield rate=68%, melting temperature=56° C.).

Example 4: Synthesis of Compound 1-D

The first compound in this example has a structure of:

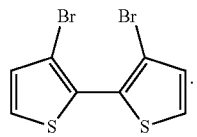 [SMILES: Brc1ccsc1-c1sccc1Br]

The second compound in this example has a structure of:

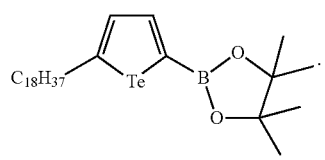

Example 5: Synthesis of Compound 1-E

The first compound in this example has a structure of:

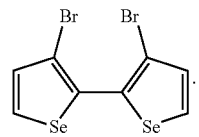 [SMILES: Brc1cc[se]c1-c1[se]ccc1Br]

The second compound in this example has a structure of:

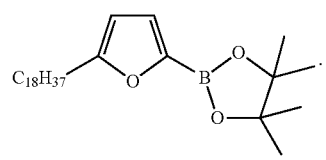

The third compound in this example has a structure of:

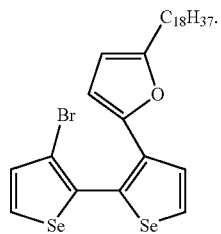

In this example, a degassed solution of the first compound (433 mg, 1.04 mmol), the second compound (463 mg, 1.04 mmol), Pd(PPh$_3$)$_4$ catalyst (60 mg, 5 mol %) and Na$_2$CO$_3$ (440 mg, 4.15 mmol) in THF/H$_2$O (29 mL/7 mL) was stirred for 17 h at 80° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (184 mg, yield rate=26%, melting temperature=37° C.).

A degassed solution of the third compound (291 mg, 0.43 mmol), pivalic acid (13 mg, 0.13 mmol), Pd-IPr catalyst (14 mg, 5 mol %) and K$_2$CO$_3$ (149 mg, 1.08 mmol) in DMAc (2 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-E (61 mg, yield rate=25%, melting temperature=58° C.).

The third compound in this example has a structure of:

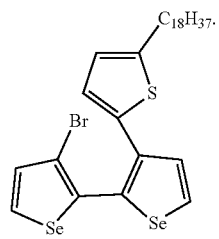

In this example, a degassed solution of the first compound (200 mg, 0.48 mmol), the second compound (222 mg, 0.48 mmol), Pd(PPh$_3$)$_4$ catalyst (28 mg, 5 mol %) and Na$_2$CO$_3$ (203 mg, 1.92 mmol) in THF/H$_2$O (14 mL/3.5 mL) was stirred for 17 h at 80° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (142 mg, yield rate=44%, melting temperature=60° C.).

A degassed solution of the third compound (142 mg, 0.21 mmol), pivalic acid (6.4 mg, 0.06 mmol), Pd-IPr catalyst (7 mg, 5 mol %) and K$_2$CO$_3$ (73 mg, 0.53 mmol) in DMAc (1 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-F (49 mg, yield rate=39%, melting temperature=70° C.).

Example 6: Synthesis of Compound 1-F

The first compound in this example has a structure of:

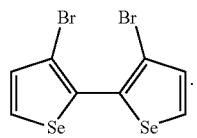 [SMILES: Brc1cc[se]c1-c1[se]ccc1Br]

The second compound in this example has a structure of:

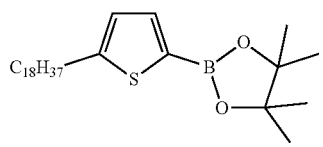

Example 7: Synthesis of Compound 1-G

The first compound in this example has a structure of:

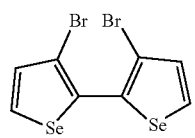

The second compound in this example has a structure of:

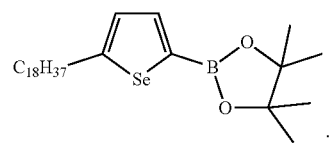

The third compound in this example has a structure of:

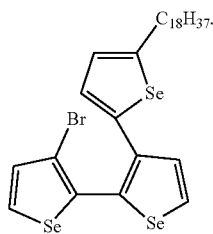

In this example, a degassed solution of the first compound (800 mg, 1.91 mmol), the second compound (975 mg, 1.91 mmol), Pd(PPh$_3$)$_4$ catalyst (111 mg, 5 mol %) and Na$_2$CO$_3$ (812 mg, 7.66 mmol) in THF/H$_2$O (55 mL/14 mL) was stirred for 17 h at 80° C. under N$_2$ atmosphere. After cooling to room temperature, the solution was extracted with ether, 30 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (760 mg, yield rate=55%, melting temperature=56° C.).

A degassed solution of the third compound (200 mg, 0.28 mmol), pivalic acid (9 mg, 0.08 mmol), Pd-IPr catalyst (9 mg, 5 mol %) and K$_2$CO$_3$ (96 mg, 0.70 mmol) in DMAc (1 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-G (109 mg, yield rate=61%, melting temperature=69° C.).

Example 8: Synthesis of Compound 1-H

The first compound in this example has a structure of:

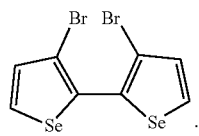 [SMILES: Brc1cc[se]c1-c1[se]ccc1Br]

The second compound in this example has a structure of:

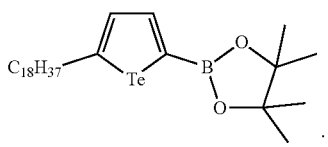

The third compound in this example has a structure of:

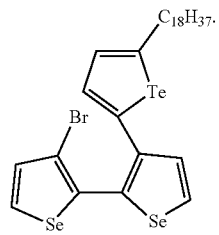

In this example, a degassed solution of the first compound (300 mg, 0.72 mmol), the second compound (427 mg, 0.72 mmol), Pd(PPh$_3$)$_4$ catalyst (41 mg, 5 mol %) and triphenylphosphine (19 mg, 0.07 mmol) in toluene (7 mL) was stirred for 17 h at 110° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a solid of the third compound (176 mg, yield rate=32%, melting temperature=58° C.).

A degassed solution of the third compound (163 mg, 0.24 mmol), pivalic acid (7.4 mg, 0.07 mmol), Pd-IPr catalyst (23 mg, 15 mol %) and K$_2$CO$_3$ (83 mg, 0.60 mmol) in DMAc (1 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 1-H (80 mg, yield rate=48%, melting temperature=63° C.).

In addition, the present invention provides a synthesis method of an asymmetric benzotrichalcogenophene compound including steps of: mixing a first compound, a second compound and a zero-valent palladium catalyst. Specifically, the zero-valent palladium catalyst is used to catalyze the Stille coupling reaction of the first compound and the second compound to form a third compound. The first compound has a structure of chemical formula (5):

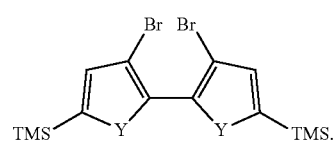

(5)

Y is selected from the group consisting of oxygen, sulfur, selenium, tellurium, and a combination thereof, and TMS is trimethylsilyl. The second compound has a structure of chemical formula (6):

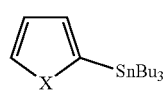

(6)

X is selected from the group consisting of oxygen, sulfur, selenium, tellurium, and a combination thereof. When Y is sulfur, X is not sulfur, SnBu$_3$ is 2-tributylstannyl.

In one embodiment, the zero-valent palladium catalyst is Pd(PPh$_3$)$_4$. In one embodiment, the method further includes dissolving the first compound, the second compound, and the zero-valent palladium catalyst in an organic solvent. The organic solvent is toluene, for example.

Aluminium chloride and acyl chloride having substituent of —COC$_q$H$_{2q+1}$ or —COOC$_r$H$_{2r+1}$ are added in succession in the next step, and q is an integer of 1-12, and r is an integer of 1~12. More specifically, aluminium chloride and acyl chloride are used to carry out the Friedel-Crafts acylation of the product formed from the first compound and the second compound. Therefore, the product may be modified with a ketone group or an alcohol group. In one embodiment, the product is dissolved in dichloromethane before adding acyl chloride and aluminium chloride into the solution.

Next, a quaternary ammonium salt is added to a solution containing the modified product to form a third compound. More specifically, the quaternary ammonium salt is used to carry out the desilylation reaction of the modified product to form the third compound. The third compound has a structure of chemical formula (7):

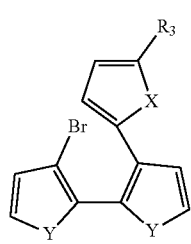

(7)

R$_3$ is —COC$_q$H$_{2q+1}$ or —COOC$_r$H$_{2r+1}$, q is an integer of 1-12, and r is an integer of 1~12.

In one embodiment, the quaternary ammonium salt is tetrabutylammonium fluoride (TBAF). In one embodiment, the modified product is dissolved in tetrahydrofuran before adding the quaternary ammonium salt.

Next, the third compound and a divalent palladium catalyst are mixed to form the asymmetric benzotrichalcogenophene compound. More specifically, the divalent palladium catalyst may catalyze the intramolecular cyclization reaction of the third compound.

In one embodiment, the divalent palladium catalyst is Pd-IPr. In one embodiment, pivalic acid and potassium carbonate are further added into the mixture while mixing the third compound and the divalent palladium catalyst. In one embodiment, an organic solvent is further added into the mixture while mixing the third compound and the divalent palladium. The organic solvent is dimethylacetamide (DMAc). In one embodiment, a mixture comprising the third compound and the divalent palladium catalyst is heated to 90~150° C. to enhance the reaction rate of the formation of the asymmetric benzotrichalcogenophene compound.

Asymmetric benzotrichalcogenophene compounds prepared by the aforementioned synthesis method are listed in Table 2:

TABLE 2

| Compound | Structure |
|---|---|
| 2-A | C$_9$H$_{19}$-CO- (furan fused with dithiophene) |
| 2-B | C$_9$H$_{19}$-CO- (thiophene fused with dithiophene) |
| 2-C | C$_9$H$_{19}$-CO- (selenophene fused with dithiophene) |
| 2-D | C$_9$H$_{19}$-CO- (tellurophene fused with dithiophene) |
| 2-E | C$_9$H$_{19}$-CO- (furan fused with diselenophene) |
| 2-F | C$_9$H$_{19}$-CO- (thiophene fused with diselenophene) |

TABLE 2-continued

| Compound | Structure |
|---|---|
| 2-G | 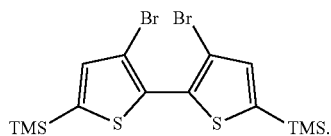 |
| 2-H | 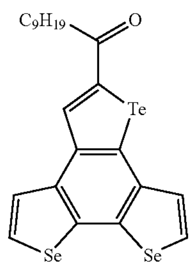 |

The reaction conditions for the synthesis of Compound 2-A to Compound 2-H are illustrated below by Examples 9-16 to describe the details of the present embodiment.

Example 9: Synthesis of Compound 2-A

The first compound in this example has a structure of:

The second compound in this example has a structure of:

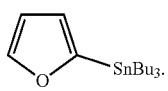

The third compound in this example has a structure of:

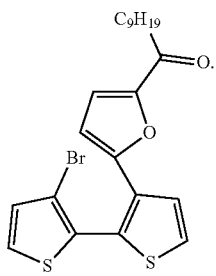

A degassed solution of the first compound (532 g, 1.14 mmol), the second compound (406 mg, 1.14 mmol), Pd(PPh$_3$)$_4$ (66 mg, 5 mol %) in toluene (11 mL) was stirred for 17 h at 110° C. under N$_2$ atmosphere. After cooling to room temperature, the solution was extracted with 10 mL ether for three times and 20 mL water for once. The combined organic layer was dried over MgSO$_4$. After removal of the organic solvent under reduced pressure and a concentration process, the residue was purified by column chromatography on silica gel (hexane) to give a liquid of 310 mg, which has a yield rate of 60%.

Aluminium chloride (136 mg, 1.02 mmol) was added into an ice-cooled solution containing the liquid (310 mg, 0.68 mmol) and decanoyl chloride (142 mg, 0.74 mmol) in dichloromethane (7 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (7 mL). A 1 M solution of TBAF in THF (0.68 mL, 0.68 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give an oil form of the third compound (164 mg, yield rate=52%).

A degassed solution of the third compound (122 mg, 0.26 mmol), pivalic acid (8 mg, 0.08 mmol), Pd-IPr catalyst (8 mg, 5 mol %) and K$_2$CO$_3$ (91 mg, 0.66 mmol) in DMAc (1 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 2-A (46 mg, yield rate=46%, melting temperature=57° C.).

Example 10: Synthesis of Compound 2-B

The first compound in this example has a structure of:

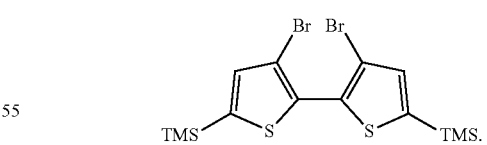

The second compound in this example has a structure of:

The third compound in this example has a structure of:

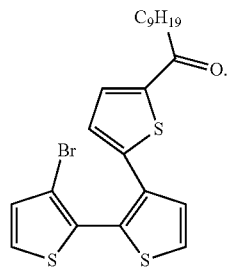

A degassed solution of the first compound (1.08 g, 2.31 mmol), the second compound (858 mg, 2.30 mmol), Pd(PPh$_3$)$_4$ (133 mg, 5 mol %) in toluene (23 mL) was stirred for 17 h at 110° C. under N$_2$ atmosphere. After cooling to room temperature, the solution was extracted with ether, 20 mL each time for three times, and once with water (30 mL). The combined organic layer was dried over MgSO$_4$. After removal of the organic solvent under reduced pressure and a concentration process, the residue was purified by column chromatography on silica gel (hexane) to give a white solid (565 mg, yield rate=52%, melting temperature=104° C.).

Aluminium chloride (148 mg, 1.5 mmol) was added into an ice-cooled solution of the white solid (350 mg, 0.74 mmol) and decanoyl chloride (156 mg, 0.82 mmol) in dichloromethane (8 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (8 mL). A 1 M solution of TBAF in THF (0.74 mL, 0.74 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give an solid of the third compound (252 mg, yield rate=71%, melting temperature=49° C.).

A degassed solution of the third compound (463 mg, 0.96 mmol), pivalic acid (29 mg, 0.19 mmol), Pd-IPr catalyst (31 mg, 5 mol %) and K$_2$CO$_3$ (332 mg, 2.41 mmol) in DMAc (4 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 2-B (262 mg, yield rate=68%, melting temperature=77° C.).

Example 11: Synthesis of Compound 2-C

The first compound in this example has a structure of:

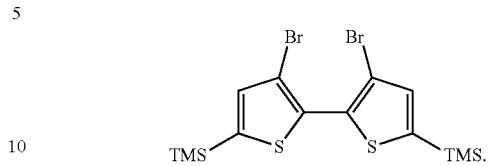

The second compound in this example has a structure of:

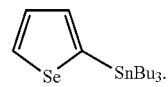

The third compound in this example has a structure of:

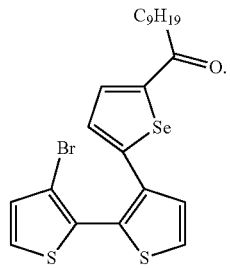

A degassed solution of the first compound (1.05 g, 2.24 mmol), the second compound (942 mg, 2.24 mmol), Pd(PPh$_3$)$_4$ (130 mg, 5 mol %) in toluene (22 mL) was stirred for 17 h at 110° C. under N$_2$ atmosphere. After cooling to room temperature, the solution was extracted with ether, 20 mL each time for three times, and once with water (30 mL). The combined organic layer was dried over MgSO$_4$. After removal of the organic solvent under reduced pressure and a concentration process, the residue was purified by column chromatography on silica gel (hexane) to give a white solid (662 mg, yield rate=57%, melting temperature=114° C.).

Aluminium chloride (170 mg, 1.27 mmol) was added into an ice-cooled solution of the solid (440 mg, 0.85 mmol) and decanoyl chloride (178 mg, 0.93 mmol) in dichloromethane (8.5 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (8.5 mL). A 1 M solution of TBAF in THF (0.85 mL, 0.85 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give a solid of the third compound (360 mg, yield rate=80%, melting temperature=58° C.).

A degassed solution of the third compound (335 mg, 0.63 mmol), pivalic acid (19 mg, 0.19 mmol), Pd-IPr catalyst (21 mg, 5 mol %) and K$_2$CO$_3$ (219 mg, 1.58 mmol) in DMAc (3 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a yellow solid of Compound 2-C (160 mg, yield rate=56%, melting temperature=86° C.).

Example 12: Synthesis of Compound 2-D

The first compound in this example has a structure of:

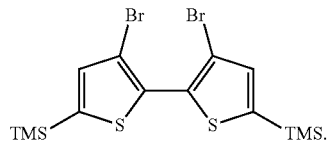 [SMILES: C[Si](C)(C)c1cc(Br)c(-c2sc([Si](C)(C)C)cc2Br)s1]

The second compound in this example has a structure of:

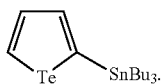

The third compound in this example has a structure of:

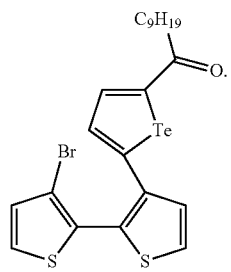

A degassed solution of the first compound (1.46 g, 3.11 mmol), the second compound (1.46 mg, 3.12 mmol), tri-tert-butylphosphine (126 mg, 0.62 mmol), Pd(PPh$_3$)$_4$ (180 mg, 5 mol %) in toluene (31 mL) was stirred for 17 h at 110° C. under N$_2$ atmosphere. After cooling to room temperature, the solution was extracted with ether, 10 mL each time for three times, and once with water (30 mL). The combined organic layer was dried over MgSO$_4$. After removal of the organic solvent under reduced pressure and a concentration process, the residue was purified by column chromatography on silica gel (hexane) to give a solid (454 mg, yield rate=26%, melting temperature=97° C.).

Aluminium chloride (32 mg, 0.24 mmol) was added into an ice-cooled solution of the solid (124 mg, 0.22 mmol) and decanoyl chloride (46 mg, 0.24 mmol) in dichloromethane (2 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (2 mL). A 1 M solution of TBAF in THF (0.22 mL, 0.22 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give a solid of the third compound (48 mg, yield rate=38%, melting temperature=101° C.).

A degassed solution of the third compound (137 mg, 0.24 mmol), pivalic acid (7.2 mg, 0.07 mmol), Pd-IPr catalyst (23 mg, 15 mol %) and K$_2$CO$_3$ (82 mg, 0.59 mmol) in DMAc (1 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid of Compound 2-D (93 mg, yield rate=79%, melting temperature=87° C.).

Example 13: Synthesis of Compound 2-E

The first compound in this example has a structure of:

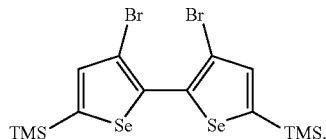 [SMILES: C[Si](C)(C)c1cc(Br)c(-c2[se]c([Si](C)(C)C)cc2Br)[se]1]

The second compound in this example has a structure of:

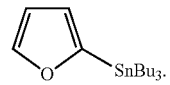

The third compound in this example has a structure of:

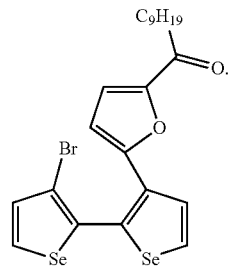

A degassed solution of the first compound (1.5 g, 2.67 mmol), the second compound (953 mg, 2.67 mmol), Pd(PPh$_3$)$_4$ (154 mg, 5 mol %) in toluene (27 mL) was stirred for 17 h at 110° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a liquid of 800 mg, which has a yield rate of 55%.

Aluminium chloride (146 mg, 1.09 mmol) was added into an ice-cooled solution containing the liquid (500 mg, 0.91 mmol) and decanoyl chloride (191 mg, 1.00 mmol) in dichloromethane (9 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (9 mL). A 1 M solution of TBAF in THF (0.91 mL, 0.91 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give an oil of the third compound (236 mg, yield rate=46%).

A degassed solution of the third compound (206 mg, 0.37 mmol), pivalic acid (11 mg, 0.11 mmol), Pd-IPr catalyst (12 mg, 5 mol %) and K$_2$CO$_3$ (128 mg, 0.93 mmol) in DMAc (1.5 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a yellow solid of Compound 2-E (35 mg, yield rate=20%, melting temperature=68° C.).

Example 14: Synthesis of Compound 2-F

The first compound in this example has a structure of:

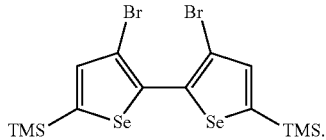 [SMILES: C[Si](C)(C)c1cc(Br)c(-c2[se]c([Si](C)(C)C)cc2Br)[se]1]

The second compound in this example has a structure of:

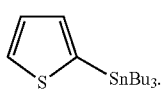

The third compound in this example has a structure of:

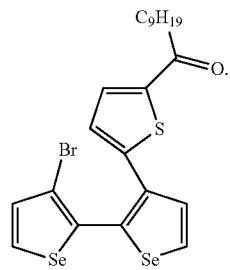

A degassed solution of the first compound (200 g, 0.36 mmol), the second compound (133 mg, 0.36 mmol), Pd(PPh$_3$)$_4$ (21 mg, 5 mol %) in toluene (4 mL) was stirred for 17 h at 110° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a white solid (113 mg, yield rate=56%, melting temperature=115° C.).

Aluminium chloride (152 mg, 1.14 mmol) was added into an ice-cooled solution of the white solid (429 mg, 0.76 mmol) and decanoyl chloride (159 mg, 0.83 mmol) in dichloromethane (8 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (8 mL). A 1 M solution of TBAF in THF (0.76 mL, 0.76 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give a solid of the third compound (252 mg, yield rate=58%, melting temperature=53° C.).

A degassed solution of the third compound (252 mg, 0.44 mmol), pivalic acid (13 mg, 0.13 mmol), Pd-IPr catalyst (14 mg, 5 mol %) and K$_2$CO$_3$ (151 mg, 1.09 mmol) in DMAc (2 mL) was stirred for 17 h at 120° C. under N$_2$ atmosphere. After cooling to room temperature, the solution was extracted with ether, 10 mL×3 each time for three times, and once with water (20 mL). The combined organic layer was dried over MgSO$_4$. After removal of the organic solvent under reduced pressure and a concentration process, the residue was purified by column chromatography on silica gel (hexane) to give a yellow solid of Compound 2-F (53 mg, yield rate=30%, melting temperature=95° C.).

Example 15: Synthesis of Compound 2-G

The first compound in this example has a structure of:

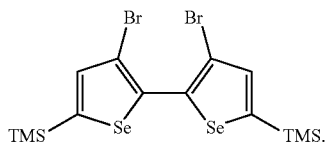 [SMILES: C[Si](C)(C)c1cc(Br)c(-c2[se]c([Si](C)(C)C)cc2Br)[se]1]

The second compound in this example has a structure of:

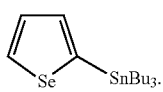

The third compound in this example has a structure of:

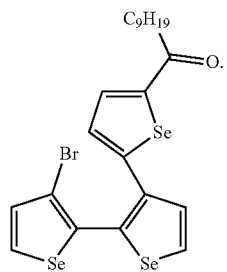

A degassed solution of the first compound (1.35 g, 2.41 mmol), the second compound (1.01 mg, 2.41 mmol), Pd(PPh$_3$)$_4$ (139 mg, 5 mol %) in toluene (24 mL) was stirred for 17 h at 110° C. under N$_2$ atmosphere. After cooling to room temperature, the solution was extracted with ether, 20 mL each time for three times, and once with water (30 mL). The combined organic layer was dried over MgSO$_4$. After removal of the organic solvent under reduced pressure and a concentration process, the residue was purified by column chromatography on silica gel (hexane) to give a white solid (707 mg, yield rate=48%, melting temperature=120° C.).

Aluminium chloride (230 mg, 1.72 mmol) was added into an ice-cooled solution of the white solid (707 mg, 1.15 mmol) and decanoyl chloride (242 mg, 1.27 mmol) in dichloromethane (12 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (12 mL). A 1 M solution of TBAF in THF (12 mL, 12 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give a solid of the third compound (510 mg, yield rate=71%, melting temperature=66° C.).

A degassed solution of the third compound (498 mg, 0.80 mmol), pivalic acid (25 mg, 0.24 mmol), Pd-IPr catalyst (26 mg, 5 mol %) and K$_2$CO$_3$ (276 mg, 2.00 mmol) in DMAc (4 mL) was stirred for 17 h at 120° C. under N$_2$ atmosphere. After cooling to room temperature, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (hexane) to give a yellow solid of Compound 2-G (140 mg, yield rate=32%, melting temperature=110° C.).

Example 16: Synthesis of Compound 2-H

The first compound in this example has a structure of:

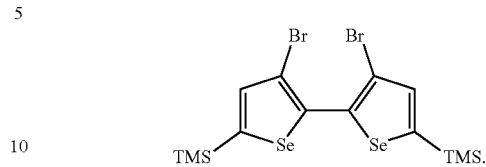

The second compound in this example has a structure of:

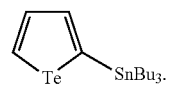

The third compound in this example has a structure of:

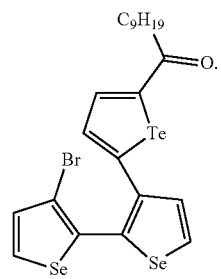

A degassed solution of the first compound (1.5 g, 2.67 mmol), the second compound (1.25 mg, 2.67 mmol), tri-tert-butylphosphine (108 mg, 0.53 mmol), Pd(PPh$_3$)$_4$ (154 mg, 5 mol %) in toluene (27 mL) was stirred for 17 h at 110° C. under N$_2$ atmosphere. After cooling to room temperature, the solution was extracted with ether, 20 mL each time for three times, and once with water (30 mL). The combined organic layer was dried over MgSO$_4$. After removal of the organic solvent under reduced pressure and a concentration process, the residue was purified by column chromatography on silica gel (hexane) to give a solid (611 mg, yield rate=35%, melting temperature=98° C.).

Aluminium chloride (35 mg, 0.26 mmol) was added into an ice-cooled solution of the solid (143 mg, 0.22 mmol) and decanoyl chloride (45 mg, 0.24 mmol) in dichloromethane (2 mL). The reaction mixture was stirred for 1 h in room temperature and extracted with dichloromethane, 10 mL each time for three times, and once with water (20 mL). The combined organic layer was dried over MgSO$_4$. After removal of the organic solvent under reduced pressure and a concentration process, the residue was dissolved in THF (2 mL). A 1 M solution of TBAF in THF (0.22 mL, 0.22 mmol) was added to the above mixture dropwise at room temperature. After stirring for 30 min, the solution was extracted with ether, 10 mL each time for three times, and once with water (20 mL). The combined organic layer was dried over MgSO$_4$. After removal of the organic solvent under reduced pressure and a concentration process, the residue was purified by column chromatography on silica gel (elution solution: ethyl acetate/hexane=1/30) to give a solid of the third compound (53 mg, yield rate=37%, melting temperature=107° C.).

A degassed solution of the third compound (102 mg, 0.15 mmol), pivalic acid (4.6 mg, 0.05 mmol), Pd-IPr catalyst (30 mg, 30 mol %) and $K_2CO_3$ (53 mg, 0.38 mmol) in DMAc (1 mL) was stirred for 17 h at 120° C. under $N_2$ atmosphere. After cooling to room temperature, the solution was extracted with ether, 10 mL each time for three times, and once with water (20 mL). The combined organic layer was dried over $MgSO_4$. After removal of the organic solvent under reduced pressure and a concentration process, the residue was purified by column chromatography on silica gel (hexane) to give a yellow solid of Compound 2-H (27 mg, yield rate=30%, melting temperature=90° C.).

Compound 1-A to Compound 2-H may be synthesized by the procedures shown in Example 1-16 respectively. The structures of Compound 1-A to Compound 2-H are further analyzed by Nuclear Magnetic Resonance (NMR), Ultra-violet-Visible Spectrophotometry (UV-Vis), and electrochemical analysis.

First, the structures of Compound 1-A to Compound 2-H are analyzed by using a MHzVarian-400 MHz nuclear magnetic resonance spectrometer with a chemical shift unit of ppm, wherein the solvent is deuterated chloroform (d-chloroform, $CDCl_3$). The internal reference of the hydrogen spectrum (δ) is 7.26 ppm ($CDCl_3$). The internal reference of the carbon spectrum (δ) is 77.00 ppm ($CDCl_3$). In Table 3, a symbol "s" represents a singlet, "d" represents a doublet, "dd" represents a doublet of doublet, "t" represents a triplet, "m" represents a multiplet, and "br" represents a broad.

The NMR data of Compound 1-A to Compound 2-H are shown in Table 3.

TABLE 3

| Compound | $^1$H NMR (400 MHz, $CDCl_3$) | $^{13}$C NMR (100 MHz, $CDCl_3$) |
|---|---|---|
| 1-A | δ 0.88 (t, J = 6.8 Hz, 3H), 1.26-1.42 (m, 28H), 1.43-1.44 (m, 2H), 1.80-1.84 (m, 2H), 2.89 (t, J = 7.6 Hz, 2H), 6.74 (s, 1H), 7.45 (d, J = 5.2 Hz, 1H), 7.48 (d, J = 5.6 Hz, 1H), 7.58 (d, J = 5.2 Hz, 1H), 7.71 (d, J = 5.6 Hz, 1H) | δ 14.1, 22.7, 28.0, 28.5, 29.2, 29.37, 29.39, 29.6, 29.7, 31.9, 101.3, 119.8, 120.1, 122.5, 124.0, 124.4, 124.6, 128.6, 129.8, 130.5, 147.6, 158.0 |
| 1-B | δ 0.89 (t, J = 6.8 Hz, 3H), 1.26-1.38 (m, 30H), 1.42-1.46 (m, 2H), 1.80-1.84 (m, 2H), 3.01 (t, J = 7.4 Hz, 2H), 7.42 (s, 1H), 7.46-7.49 (m, 2H), 7.55 (d, J = 5.6 Mz, 1H), 7.69 (d, J = 5.6 Mz, 1H) | δ 14.1, 22.7, 29.1, 29.37, 29.4, 29.6, 29.67, 29.7, 30.8, 31.5, 31.9, 119.4, 122.3, 122.7, 124.0, 124.7, 129.7, 130.8, 131.0, 131.5, 132.3, 132.8, 145.4 |
| 1-C | δ 0.89 (t, J = 6.8 Mz, 3H), 1.26-1.38 (m, 28H), 1.43-1.47 (m, 2H), 1.78-1.82 (m, 2H) 3.05 (t, J = 7.6 Mz, 2H), 7.44-7.48 (m, 3H), 7.63 (s, 1H), 7.68 (d, J = 5.2 Mz, 1H) | δ 14.1, 22.7, 29.1, 29.4, 29.44, 29.6, 29.7, 29.73, 32.0, 32.4, 33.3, 122.7, 123.0, 123.5, 124.0, 124.8, 129.6, 131.1, 133.3, 133.8, 134.0, 134.8, 150.8 |
| 1-D | δ 0.88 (t, J = 6.8 Hz, 3H), 1.26-1.36 (m, 28H), 1.44-1.46 (m, 2H), 1.72-1.74 (m, 2H), 3.02 (t, J = 7.6 Mz, 2H), 7.27 (d, J = 5.2 Hz, 1H), 7.42 (d, J = 5.6 Hz, 1H), 7.45 (d, J = 5.2 Mz, 1H), 7.71 (d, J = 5.6 Mz, 1H), 8.05 (s, 1H) | δ 14.2, 22.8, 29.2, 29.4, 29.5, 29.6, 29.7, 29.8, 32.0, 34.2, 37.3, 123.6, 123.9, 124.7, 125.4, 125.7, 129.0, 131.1, 132.0, 135.9, 138.9, 140.5, 147.6 |
| 1-E | δ 0.88 (t, J = 6.6 Mz, 3H), 1.26-1.40 (m, 28H), 1.42-1.43 (m, 2H), 1.78-1.83 (m, 2H), 2.87 (t, J = 7.6 Mz, 2H), 6.71 (s, 1H), 7.83 (d, J = 6 Mz, 1H), 7.97-8.04 (m, 3H) | δ 14.1, 22.7, 28.0, 28.5, 29.2, 29.38, 29.4, 29.6, 29.7, 29.72, 31.9, 101.4, 122.2, 123.4, 125.5, 126.1, 127.7, 127.8, 132.2, 132.9, 134.1, 149.3, 158.0 |
| 1-F | δ 0.88 (t, J = 6.6 Mz, 3H), 1.25-1.45 (m, 30H), 1.79-1.83 (m, 2H), 2.99 (t, J = 7.6 Mz, 2H), 7.41 (s, 1H), 7.81 (d, J = 6 Mz, 1H), 7.96 (d, J = 6 Mz, 1H), 8.02-8.06 (m, 2H) | δ 14.1, 22.7, 29.1, 29.38, 29.4, 29.6, 29.68, 29.7, 30.8, 31.5, 31.9, 119.6, 126.0, 126.4, 127.3, 128.1, 133.0, 133.2, 134.0, 134.4, 134.6, 135.6, 145.3 |
| 1-G | δ 0.89 (t, J = 6.8 Mz, 3H), 1.26-1.46 (m, 30H), 1.76-1.83 (m, 2H), 3.03 (t, J = 7.4 Mz, 2H), 7.62 (s, 1H), 7.69 (d, J = 6 Mz, 1H), 7.95 (d, J = 6 Mz, 1H), 8.00 (d, J = 5.6 Mz, 1H), 8.03 (d, J = 5.6 Mz, 1H) | δ 14.2, 22.7, 29.1, 29.4, 29.44, 29.6, 29.68, 29.7, 29.74, 32.0, 32.3, 33.3, 123.0, 126.7, 127.3, 127.34, 128.0, 134.2, 135.2, 135.5, 135.8, 135.9, 136.5, 150.7 |
| 1-H | δ 0.88 (t, J = 6.6 Hz, 3H), 1.25-1.37 (m, 28H), 1.41-1.47 (m, 2H), 1.69-1.77 (m, 2H), 3.01 (t, J = 7.4 Mz, 2H), 7.49 (d, J = 5.6 Hz, 1H), 7.97 (d, J = 5.6 Hz, 1H), 7.99-8.01 (m, 2H), 8.04 (s, 1H) | δ 14.2, 22.8, 29.2, 29.4, 29.5, 29.6, 29.7, 29.8, 32.0, 34.2, 37.3, 127.1, 127.4, 127.45, 127.8, 129.8, 131.5, 133.7, 137.0, 137.6, 140.6, 142.2, 147.3 |
| 2-A | δ 0.88 (t, J = 6.8 Hz, 3H), 1.25-1.39 (m, 10H), 1.41-1.47 (m, 2H), 1.81-1.85 (m, 2H), 3.04 (t, J = 7.4 Hz, 2H), 7.53, (d, J = 5.2 Hz, 1H), 7.58, (d J = 5.6 Hz, | δ 14.1, 22.7, 24.5, 29.3, 29.4, 29.5, 31.9, 38.9, 112.2, 119.1, 120.5, 122.4, 123.8, 125.2, 126.0, 130.1, 131.0, 134.8, 149.7, 151.6, 190.9 |

TABLE 3-continued

| Compound | $^1$H NMR (400 MHz, CDCl$_3$) | $^{13}$C NMR (100 MHz, CDCl$_3$) |
|---|---|---|
| | 1H), 7.67, (d, J = 5.2 Hz, 1H), 7.85 (d, J = 5.2 Hz, 1H) | |
| 2-B | δ 0.88 (t, J = 5.8 Hz, 3H), 1.29-1.37 (m, 10H,), 1.41-1.45 (m, 2H), 1.80-1.85 (m, 2H), 3.07 (t, J = 7.6 Hz, 2H), 7.53-7.56 (m, 2H), 7.64 (d, J = 5.2 Hz, 1H), 7.76 (d, J = 5.2 Mz, 1H), 8.32 (s, 1H) | δ14.1, 22.7, 24.8, 29.3, 29.4, 29.5, 31.9, 39.4, 122.4, 122.6, 125.2, 125.4, 127.0, 131.0, 131.5, 132.1, 133.1, 133.4, 136.1, 142.0, 194.4 |
| 2-C | δ 0.88 (t, J = 6.4 Hz, 3H), 1.28-1.37 (m, 10H), 1.41-1.45 (m, 2H), 1.79-1.85 (m, 2H), 3.08 (t, J = 7.6 Mz, 2H), 7.53-7.57 (m, 3H), 7.78 (d, J = 5.2 Hz, 1H), 8.58 (s, 1H) | δ 14.1, 22.7, 24.9, 29.3, 29.4, 29.5, 31.9, 38.7, 122.6, 123.9, 125.2, 125.4, 130.5, 131.8, 133.0, 133.7, 134.4, 134.8, 138.7, 147.3, 195.4 |
| 2-D | δ 0.88 (t, J = 6.8 Hz, 3H), 1.26-1.39 (m, 10H), 1.41-1.45 (m, 2H), 1.80-1.84 (m, 2H), 3.09 (t, J = 7.4 Mz, 2H), 7.35 (d, J = 5.6 Hz, 1H), 7.49-7.51 (m, 2H), 7.79 (d, J = 5.2 Hz, 1H), 9.02 (s, 1H) | δ14.1, 22.7, 25.1, 29.3, 29.5, 29.51, 29.53, 31.9, 37.5, 123.1, 124.9, 125.2, 126.1, 131.9, 132.0, 132.3, 137.2, 138.5, 138.7, 140.7, 146.1, 198.0 |
| 2-E | δ 0.88 (t, J = 6.8 Mz, 3H), 1.28-1.39 (m, 10H), 1.41-1.45 (m, 2H), 1.81-1.84 (m, 2H), 3.02 (t, J = 7.4 Mz, 2H), 7.83 (s, 1H), 7.91 (d, J = 5.6 Mz, 1H), 8.10-8.11 (m, 2H), 8.16 (d, J = 5.6 Mz, 1H) | δ 14.1, 22.7, 24.5, 29.3, 29.4, 29.5, 31.9, 38.9, 112.1, 120.7, 123.6, 125.4, 125.7, 128.8, 129.7, 132.7, 134.7, 139.7, 150.9, 151.2, 191.0 |
| 2-F | δ 0.88 (t, J = 6.8 Hz, 3H), 1.25-1.45 (m, 12H), 1.82-1.85 (m, 2H), 3.06 (t, J = 7.6 Mz, 1H), 7.89 (d, J = 5.6 Mz, 1H), 8.04 (d, J = 5.6 Hz, 1H), 8.12 (d, J = 5.6 Mz, 1H), 8.14 (d, J = 5.6 Mz, 1H), 8.31 (s, 1H) | δ 14.1, 22.7, 24.8, 29.3, 29.4, 29.5, 31.9, 39.4, 126.0, 126.1, 127.3, 129.0, 129.1, 132.9, 133.8, 135.0, 136.7, 137.7, 138.9, 141.8, 194.6 |
| 2-G | δ 0.88 (t, J = 6.4 Hz, 3H), 1.29-1.39 (m, 10H), 1.41-1.45 (m, 2H), 1.81-1.84 (m, 2H), 3.06 (t, J = 7.4 Mz, 2H), 7.78 (d, J = 5.6 Hz, 1H), 8.05 (d, J = 5.6 Hz, 1H), 8.09-8.13 (m, 2H), 8.56 (s, 1H) | δ14.1, 22.7, 24.9, 29.4, 29.5, 29.52, 31.9, 38.7, 126.2, 127.4, 128.7, 128.8, 130.8, 135.5, 136.0, 136.6, 136.8, 138.4, 140.1, 146.9, 195.5 |
| 2-H | δ 0.88 (t, J = 6.6 Hz, 3H), 1.29-1.41 (m, 10H), 1.43-1.45 (m, 2H), 1.80-1.84 (m, 2H), 3.09 (t, J = 7.4 Hz, 2H), 7.59 (d, J = 5.6 Hz, 1H), 8.06-8.10 (m, 3H), 9.05 (s, 1H) | δ 14.1, 22.7, 25.1, 29.3, 29.4, 29.48, 29.5, 31.9, 37.6, 126.7, 128.5, 128.6, 129.9, 133.5, 137.6, 139.1, 139.2, 140.7, 142.4, 145.8, 198.2 |

Next, using a HITACHIU-4100 UV-Visible spectrometer, the extinction coefficient of Compound 1-A to Compound 2-H are measured after dissolving Compound 1-A to Compound 2-H in a 10 M chloroform solution respectively.

Table 4 is the UV absorption data of Compound 1-A to Compound 2-H:

TABLE 4

| Compound | Absorption wavelength $\lambda_{max}$ (nm) | Molecular band gap $E_g^{opt}$ (eV) |
|---|---|---|
| 1-A | 255, 304, 317, 339, 355 | 3.52 |
| 1-B | 268, 277, 302, 313, 343 | 3.55 |
| 1-C | 272, 283, 304, 315 | 3.49 |
| 1-D | 295, 321 | 3.42 |
| 1-E | 257, 304, 317, 339, 355 | 3.38 |
| 1-F | 274, 281, 311, 323, 337, 354 | 3.43 |
| 1-G | 279, 287, 312, 325, 340, 356 | 3.38 |
| 1-H | 300, 332, 361 | 3.34 |
| 2-A | 294, 339 | 3.36 |
| 2-B | 289, 300, 341 | 3.26 |
| 2-C | 297, 305, 351 | 3.20 |
| 2-D | 301, 307, 362 | 2.81 |
| 2-E | 289, 302, 351 | 3.26 |
| 2-F | 297, 309, 352 | 3.20 |
| 2-G | 314, 356 | 3.15 |
| 2-H | 312, 367 | 2.79 |

In the group of furan, thiophene, selenophene and tellurophene, the order of the maximum absorption wavelength is furan<thiophene<selenophene<tellurophene. Therefore, in the group of Compound 1-A~1-D, Compound 1-A has the greatest blue-shift in the UV absorption, and Compound 1-D has the greatest redshift, as shown in Table 4. Similarly, in the groups of Compound 1-E~1-H, Compound 2-A~2-D, and Compound 2-E~2-H, Compound 1-E, Compound 2-A, and Compound 2-E have the greatest blue-shift respectively, while Compound 1-H, Compound 2-D, and Compound 2-H have the greatest redshift respectively.

It is known that —COC$_9$H$_{19}$ group may reduce molecular band gap due to its electron-withdrawing tendency. Therefore, as shown in Table 4, the molecular band gap of Compound 2-A to Compound 2-H are lower than Compound 1-A to Compound 1-H, as Compound 2-A to Compound 2-H have —COC$_9$H$_{19}$ group, while Compound 1-A to Compound 1-H have —C$_{18}$H$_{37}$ group.

The highest occupied molecular orbital (HOMO) energy level, the lowest unoccupied molecular orbital (LUMO) energy level, and the oxidation potential of Compound 1-A to Compound 2-H are measured using the CH Instruments Model 600D series electrochemical analyzer. The electrolytic solution is a 0.1 M solution of tetrabutylammonium hexafluorophosphate (TBAPF$_6$) in acetonitrile. A 0.01 M silver nitrate solution and a 0.1 M solution of tetrabutylammonium perchlorate (TBAP) in acetonitrile are added to the Ag/Ag$^+$ reference electrode. The solution containing Compound 1-A to Compound 2-H are coated on the working electrode, respectively. The scanning rate is 80 mV/s, and the internal reference potential is ferrocene/ferrocenium (Fc/Fc$^+$).

The HOMO energy levels, the LOMO energy levels and the oxidation potentials of Compound 1-A to Compound 2-H are shown in Table 5:

TABLE 5

| Compound | HOMO (eV) | LUMO (eV) | $E_{ox}^{onset}$ (eV) |
|---|---|---|---|
| 1-A | −5.69 | −2.17 | 0.89 |
| 1-B | −5.90 | −2.35 | 1.10 |
| 1-C | −5.89 | −2.40 | 1.09 |
| 1-D | −5.39 | −1.97 | 0.59 |
| 1-E | −5.63 | −2.25 | 0.83 |
| 1-F | −5.68 | −2.25 | 0.88 |
| 1-G | −5.62 | −2.24 | 0.82 |
| 1-H | −5.38 | −2.04 | 0.58 |
| 2-A | −5.94 | −2.58 | 1.14 |
| 2-B | −5.91 | −2.63 | 1.11 |
| 2-C | −5.90 | −2.68 | 1.10 |
| 2-D | −5.51 | −2.70 | 0.71 |
| 2-E | −5.89 | −2.63 | 1.09 |
| 2-F | −5.84 | −2.64 | 1.04 |
| 2-G | −5.81 | −2.66 | 1.01 |
| 2-H | −5.43 | −2.64 | 0.63 |

It is known that the oxidation potential of selenophene is lower than thiophene, and the HOMO energy level of selenophene is higher than thiophene. Therefore, the HOMO energy levels of compounds 1-E to Compound 1-H are higher than compounds 1-A to Compound 1-D. Similarly, the HOMO energy level of Compound 2-E to Compound 2-H are higher than Compound 2-A to Compound 2-D.

Since —COC$_9$H$_{19}$ group may reduce the HOMO/LUMO energy levels due to its electron-withdrawing tendency, the HOMO/LUMO energy levels of Compound 2-A to Compound 2-H are lower than Compound 1-A to Compound 1-H, as Compound 2-A to Compound 2-H have —COC$_9$H$_{19}$ group, while Compound 1-A to Compound 1-H have —C$_{18}$H$_{37}$ group.

It is noted that, the asymmetric benzotrichalcogenophene compound may further polymerize with an electron-accepting compound to form a polymer. The polymer may be used as a semiconductor active layer material in an organic field effect transistor. In addition, the polymer can serve as a heterogeneous interface material of an organic solar cell.

In one embodiment, the electron-accepting compound is 3,6-bis(5-bromo-2-thienyl)-2,5-dihydro-2,5-bis(2-octyldodecyl)pyrrolo[3,4-c]pyrrole-1,4-dione (Br-DPP), 4,7-bis(5-bromothiophen-2-yl)-5,6-difluoro-2,1,3-benzothiadiazole (Br-DTFBT), Or 5,10-di(5-bromothiophen-2-yl)naphtho[1,2-c:5,6-c']bis([1,2,5]thiadiazole (Br-DTNT).

In one embodiment, the polymerizing method of the asymmetric benzotrichalcogenophene compound and the electron-accepting compound includes the successive steps of mixing the asymmetric benzotrichalcogenophene compound with n-Butyllithium (n-BuLi) to carry out the deprotonation reaction, and the reaction is terminated by the addition of trimethyltin. A palladium metal catalyst is used to catalyze the Stille coupling reaction of the product and the electron-accepting compound to form a polymer. The palladium metal catalyst is tris (dibenzylideneacetone)dipalladium (Pd$_2$(dba)$_3$), for example.

The polymer prepared by the polymerization of the asymmetric benzotrichalcogenophene compound and the electron-accepting compound has a structure of chemical formula (8):

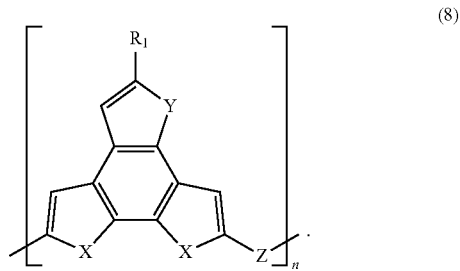

R1 is hydrogen, —C$_p$H$_{2p+1}$, —COC$_q$H$_{2q+1}$ or —COOC$_r$H$_{2r+1}$, p is an integer of 1~20, q is an integer of 1~12, r is an integer of 1~12, and n is an integer of 10~100. X is selected from the group consisting of oxygen, sulfur, selenium, tellurium, and a combination thereof. Y is selected from the group consisting of oxygen, sulfur, selenium, tellurium, and a combination thereof. Z is selected from the group consisting of

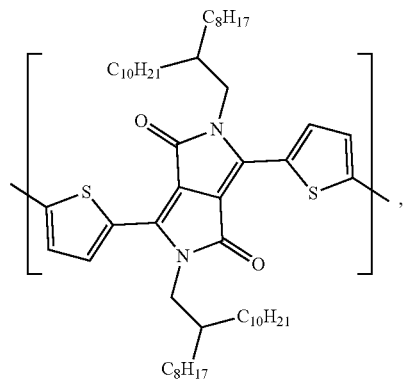

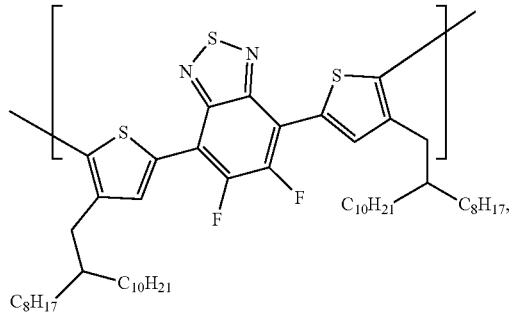

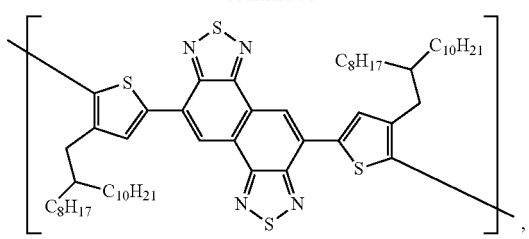

combination thereof.

The following examples describe a Polymer I synthesized from Compound 1-B and Br-DPP, a Polymer II synthesized from Compound 1-G and Br-DPP, a Polymer III synthesized from Compound 1-B and Br-DTFBT, a Polymer IV synthesized from Compound 1-G and Br-DTFBT, and a Polymer V synthesized from Compound 1-G and Br-DTNT.

In one example, a deprotonation reaction of Compound 1-B is carried out by adding n-butyllithium. The reaction is terminated by adding trimethyltin chloride. $Pd_2(dba)_3$ is used to catalyze the Stille coupling reaction of the product and Br-DPP to form Polymer I. Polymer I has a structure as follows:

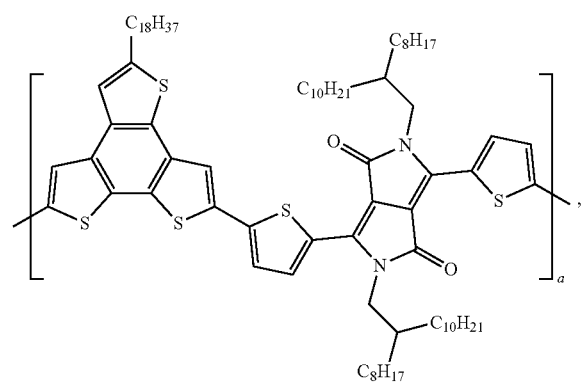

and a is 60.

The nuclear magnetic resonance data of Polymer I is: $^1$H NMR (400 MHz, $CDCl_3$) δ 0.81-0.90 (br, 15H), 1.25-1.82 (br, 100H), 3.31-3.53 (br, 4H), 6.26-6.79 (br, 3H), 7.52-7.78 (br, 2H), 8.63-9.50 (br, 2H).

In one example, a deprotonation reaction of Compound 1-G is carried out by adding n-butyllithium. The reaction is terminated by adding trimethyltin chloride. $Pd_2(dba)_3$ is used to catalyze the Stille coupling reaction of the product and Br-DPP to form Polymer II. Polymer II has a structure as follows:

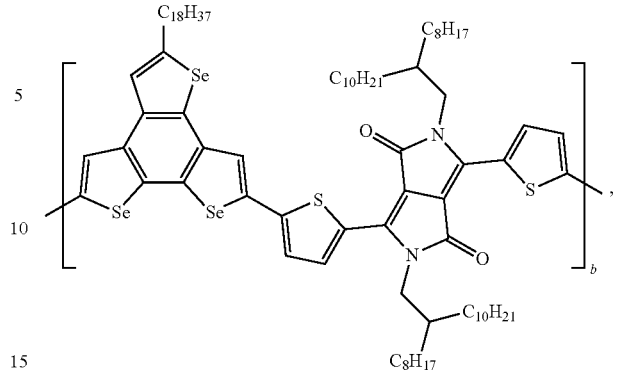

and b is 60.

The nuclear magnetic resonance data of Polymer II is: $^1$H NMR (400 MHz, $CDCl_3$) δ 0.89-1.00 (br, 15H), 1.28-1.91 (br, 100H), 3.16-3.54 (br, 4H), 6.25-7.00 (br, 3H), 7.35-7.84 (br, 2H), 8.73-9.32 (br, 2H).

In one example, a deprotonation reaction of Compound 1-B is carried out by adding n-butyllithium. The reaction is terminated by adding trimethyltin chloride. $Pd_2(dba)_3$ is used to catalyze the Stille coupling reaction of the product and Br-DTFBT to form Polymer III. Polymer III has a structure as follows:

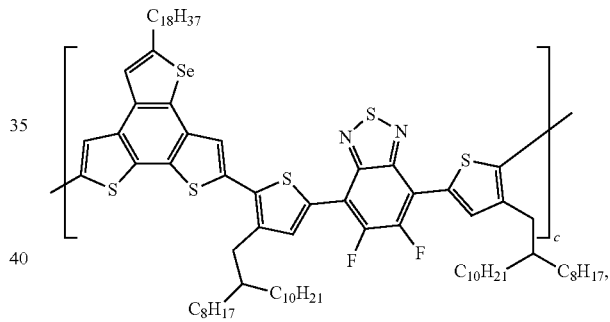

and c is 50.

In one example, a deprotonation reaction of Compound 1-G is carried out by adding n-butyllithium. The reaction is terminated by adding trimethyltin chloride. $Pd_2(dba)_3$ is used to catalyze the Stille coupling reaction of the product and Br-DTFBT to form Polymer IV. Polymer IV has a structure as follows:

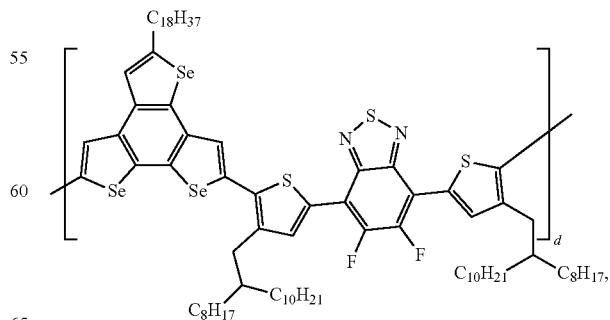

and d is 50.

In one example, a deprotonation reaction of Compound 1-G is carried out by adding n-butyllithium. The reaction is terminated by adding trimethyltin chloride. Pd$_2$(dba)$_3$ is used to catalyze the Stille coupling reaction of the product and Br-DTNT to form Polymer V. Polymer V has a structure as follows:

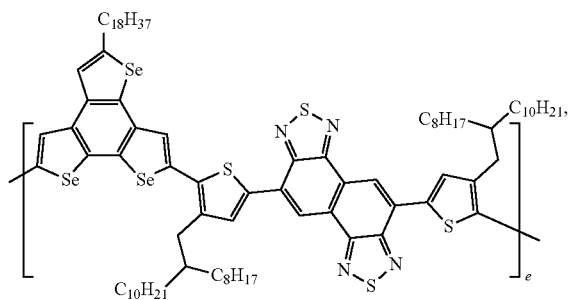

and e is 20.

The UV absorption properties of Polymer I-Polymer V are measured, wherein Polymer I-Polymer V are prepared into a solution form and a thin film form. The solution is prepared by dissolving Polymer I-Polymer V in chlorobenzene, and the thin film is prepared by spin-coating a solution containing 2 wt % of Polymer I-Polymer V on a 2.5×2.5 cm$^2$ of quartz glass. Table 6 is the UV absorption data of Polymer I-Polymer V:

TABLE 6

| Polymer | Absorption Wavelength $\lambda_{max}$ (nm) | | Optical Band Gap $E_g^{opt}$ (eV) |
| --- | --- | --- | --- |
| | Solution | thin film | |
| I | 767 | 761 | 1.46 |
| II | 787 | 786 | 1.44 |
| III | 610 | 649 | 1.75 |
| IV | 593 | — | 1.71 |
| V | 640 | 683 | 1.64 |

Since the degree of overlap of the atomic orbital of oxygen, sulfur, selenium, tellurium with the P$_z$ orbital of the carbon atom is reducing due to the increasing atomic radius, therefore the molecular band gap of oxygen, sulfur, selenium, tellurium is decreasing as well. Thus, the optical band gap of Polymer II is lower than Polymer I, as shown in Table 6. Similarly, the optical band gap of Polymer IV is lower than Polymer III.

The HOMO energy level, the LOMO energy level, and the electrochemical band gap ($E_g^{cv}$) of Polymer I~Polymer IV are shown in Table 7:

TABLE 7

| Polymer | HOMO (eV) | LUMO (eV) | electrochemical band gap $E_g^{cv}$(eV) |
| --- | --- | --- | --- |
| I | −5.51 | −3.67 | 1.84 |
| II | −5.49 | −3.67 | 1.82 |
| III | −5.90 | −3.44 | 2.46 |
| IV | −5.87 | −3.60 | 2.27 |

Since selenophene has a stronger polarizing ability than thiophene, therefore the intermolecular force of Polymer II is stronger than Polymer I, so that Polymer II has good stacking properties in the form of thin film, which enhances the HOMO level of Polymer II, resulting in a narrower electrochemical band gap, as shown in Table 7. Similarly, the electrochemical band gap of Polymer IV is narrower than Polymer III.

The performances of using Polymer I and Polymer II as the active layer material of a semiconductor are further tested, as well as the performances of using Polymer I-Polymer IV as the heterogeneous interface material of a solar cell.

The Polymer I and Polymer II are respectively spin-coated on the semiconductor active layer of a field effect transistor having a bottom-gate-top-contact structure, that is, a gate electrode is located below the semiconductor active layer, and a source electrode and a gate electrode are located above the semiconductor active layer. The performances of Polymer I and Polymer II are tested, as well as the performances after 10 minutes of heat treatment at an annealing temperature of 210° C. The tested data includes the threshold voltage ($V_{th}$), the on-off ratio ($I_{on/off}$) and the carrier mobility, as shown in Table 8:

TABLE 8

| Polymer | $V_{th}$ (V) | $I_{on/off}$ | carrier mobility (cm$^2$V$^{-1}$s$^{-1}$) |
| --- | --- | --- | --- |
| I | −14.1 | 1.76 × 10$^7$ | 0.61 |
| I (with heat treatment) | −4.12 | 5.13 × 10$^5$ | 0.18 |
| II | −5.15 | 5.20 × 10$^6$ | 0.04 |
| II (with heat treatment) | −7.6 | 1.85 × 10$^6$ | 0.17 |

As shown in Table 8, both Polymer I and Polymer II show excellent carrier mobility, regardless of being heat treated or not. Thus, Polymer I and Polymer II are suitable materials for semiconductor active layer. As the carrier mobility of Polymer I and Polymer II may be influenced by their molecular weight, therefore the carrier mobility of Polymer I is higher than Polymer II, as the molecular weight of Polymer I is higher than Polymer II.

In addition, the Polymer I-IV are mixed with [6,6]-Phenyl C71 butyric acid methyl ester (PC$_{71}$BM) in an organic solar cell, respectively. The open-circuit voltage ($V_{oc}$) (the measured voltage of a device when disconnected from any circuit), the short-circuit current ($J_{sc}$) (the current through the solar cell when the voltage across the solar cell is zero), the fill factor (FF) (the ratio of maximum obtainable power to the product of the open-circuit voltage and short-circuit current), and the power conversion efficiency (PCE) (the efficiency of a solar cell, which is measured by the ratio between the output power and the input power) of the mixed material are measured, as shown in Table 9:

TABLE 9

| Polymer | polymer:PC$_{71}$BM (wt % ratio) | $V_{oc}$ (V) | $J_{sc}$ (mA/cm$^2$) | FF (%) | PCE (%) |
| --- | --- | --- | --- | --- | --- |
| I | 1:2 | 0.64 | 15.96 | 60.07 | 6.14 |
| II | 1:2 | 0.68 | 12.01 | 71.13 | 5.81 |
| III | 1:2 | 0.74 | −7.2 | 70.50 | 3.76 |
| IV | 1:2 | 0.80 | −3.30 | 65.01 | 1.72 |

As shown in Table 9, Polymer I, II, III and IV show excellent photoelectric conversion efficiency, and therefore they are suitable heterogeneous interface materials of a solar cell.

In summary, the present invention provides an asymmetric benzotrichalcogenophene compound containing two or more types of chalcogenophene and the synthesis method thereof by the use of a Pd(PPh₃)₄ catalyst and a Pd-IPr catalyst. In addition, the asymmetric benzotrichalcogenophene compound may further polymerize with an electron-accepting compound to form a polymer having excellent carrier mobility and photoelectric conversion efficiency. The polymer can serve as a material of an organic field effect transistor or an organic solar cell.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An asymmetric benzotrichalcogenophene compound, having a structure of chemical formula (1):

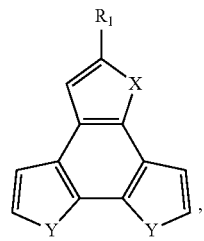

(1)

wherein $R_1$ is hydrogen, $-C_pH_{2p+1}$, $-COC_qH_{2q+1}$ or $-COOC_rH_{2r+1}$, p is an integer of 1-20, q is an integer of 1-12, r is an integer of 1-12, X is selected from the group consisting of sulfur, selenium, tellurium, and a combination thereof, Y is selected from the group consisting of oxygen, sulfur, selenium, tellurium, and a combination thereof, and when X is sulfur, Y is not sulfur.

2. The asymmetric benzotrichalcogenophene compound of claim 1, wherein $-C_pH_{2p+1}$ is a linear structure or a branched structure.

3. The asymmetric benzotrichalcogenophene compound of claim 1, wherein $-CO_qH_{2q+1}$ is a linear structure or a branched structure.

4. The asymmetric benzotrichalcogenophene compound of claim 1, wherein $-COOC_rH_{2r+1}$ is a linear structure or a branched structure.

5. A polymer, having a structure of chemical formula (8):

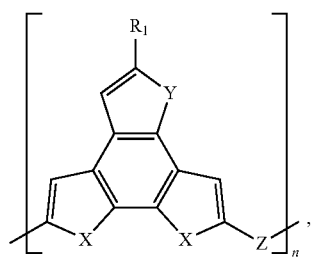

(8)

wherein $R_1$ is hydrogen, $-C_pH_{2p+1}$, $-COC_qH_{2q+1}$ or $-COOC_rH_{2r+1}$, p is an integer of 1~20, q is an integer of 1~12, r is an integer of 1~12, n is an integer of 10~100, X is selected from the group consisting of oxygen, sulfur, selenium, and tellurium, and a combination thereof, Y is selected from the group consisting of oxygen, sulfur, selenium, and tellurium, and a combination thereof, Z is selected from the group consisting of

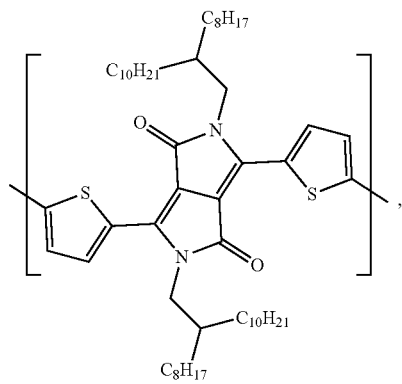

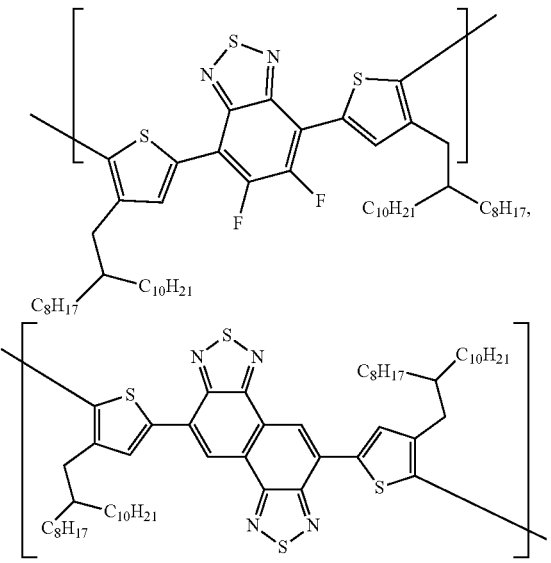

and a combination thereof.

* * * * *